United States Patent [19]

Wascher et al.

[11] Patent Number: 5,041,136
[45] Date of Patent: Aug. 20, 1991

[54] IMPLANTABLE ARTIFICIAL SOFT BLADDER SYSTEM

[75] Inventors: Uwe Wascher, Lenox, Mass.; Jacek L. Mostwin, Baltimore, Md.; Lorne Belden, Jr., Louisville, Ky.; Gerald Kushner, Louisville, Ky.; Louis W. Hardin, Louisville, Ky.

[73] Assignee: General Electric Company, Pittsfield, Mass.

[21] Appl. No.: 428,296

[22] Filed: Oct. 27, 1989

[51] Int. Cl.$^5$ .................................. A61F 2/04
[52] U.S. Cl. .............................. 623/12; 600/30; 128/DIG. 25
[58] Field of Search ............ 623/12; 600/29-32; 128/DIG. 25

[56] References Cited

U.S. PATENT DOCUMENTS

| | | | |
|---|---|---|---|
| 3,953,897 | 5/1976 | Chevallet | 623/12 |
| 4,044,401 | 8/1977 | Guiset | 623/12 |
| 4,228,550 | 10/1980 | Salkind | 623/12 X |
| 4,311,659 | 2/1985 | Rey et al. | 623/66 X |
| 4,497,074 | 2/1985 | Rey et al. | 623/12 |
| 4,711,231 | 12/1987 | Finegold et al. | 128/DIG. 25 X |
| 4,781,176 | 11/1988 | Ravo | 623/12 |
| 4,961,747 | 10/1990 | Wascher et al. | 623/12 |

FOREIGN PATENT DOCUMENTS

| | | | |
|---|---|---|---|
| 2655034 | 6/1978 | Fed. Rep. of Germany | 623/12 |
| 2116838 | 7/1972 | France | 623/12 |
| 0181242 | 4/1966 | U.S.S.R. | 623/12 |

Primary Examiner—David J. Isabella
Assistant Examiner—David H. Willse
Attorney, Agent, or Firm—Hedman, Gibson, Costigan & Hoare

[57] ABSTRACT

An implantable artificial bladder soft system is provided which comprises an at least partially deformation resistant support base, a compliant deformable diaphragm, an inlet means, an outlet means, an optional outer shell, an optional backflow control means, an optional discharge control means, and an optional anchoring means. This implantable artificial bladder can be completely emptied. A method for the collection of, the storage of and the discharge of biological fluids incorporating the implantable artificial bladder soft system is provided as well.

25 Claims, 1 Drawing Sheet

IMPLANTABLE ARTIFICIAL SOFT BLADDER SYSTEM

This invention relates to an implantable artificial bladder for the collection of, the storage of, or the discharge of biological fluids, more specifically urine, in a patient whose natural bladder has failed or has been removed.

BACKGROUND OF THE INVENTION

Loss of the urinary bladder, most commonly due to total cystectomy for muscle invasive carcinoma of the bladder, bladder dysfunction or bladder injury resulting in contraction, stiffness, spasticity or failure to store or to empty urine in a suitable manner are presently being treated with replacement or augmentation of the urinary bladder with intestinal tissue. These operations all have in common either the creation of an intestinal urinary conduit which drains urine continuously into a plastic bag on the patient's abdominal wall or the creation of an internal pouch constructed of intestinal tissue which stores urine inside the patient's abdominal cavity, urine being released either by catheter or newly learned techniques of urination which rely on coordinated abdominal muscle contraction and pelvic muscle relaxation.

Although the simplest of these forms of urinary diversion, the Bricker intestinal conduit or "ileal loop", is a standard and commonly performed surgical procedure, it is the least desirable. A bag must be worn on the abdominal wall which leads to social withdrawal and undesirable change in body image and has been shown to lead to long term damage of the kidneys from infection, obstruction and urinary stone formation.

There has been great interest and activity, as an alternative to this kind of diversion, in the construction of internal urinary reservoirs made of long segments of intestinal tissue. These operations are difficult to perform and usually can be done only in specialized medical centers. There is a considerable increase in risk to the patient. Normal urination will only be possible in a very small select group of men in whom the pouch can be sewn to the natural urinary outlet. In the remaining group of patients, which includes all women, the reservoir must be emptied by intermittent self catheterization introduced by way of an opening in the abdominal wall or the perineum. In addition to the potential for operative complications, the long term effects of redirecting a long segment of intestine from the intestinal tract to a reservoir which provides continuous contact with urine has yet to be determined. Disorders of digestive motility and absorption are common, absorption of urinary waste products through the intestinal wall is common, and the potential for development of cancer in the bowel segment in continuous contact with urine has been recognized, although the extent to which this may become a problem is yet unknown.

Although the use of extensive intestinal substitution and augmentation of the urinary bladder has become popular and safe in the hands of very specialized urological surgeons in a few national medical centers, the long term safety and efficacy remains to be determined, and there is every reason to believe that unexpected difficulties may arise within the next ten years following such reconstruction. There is thus a great need for a totally artificial urinary bladder which would allow patients to undergo complete replacement of the bladder without removal of any segment of the digestive tract.

Sowinski, French Patent No. 2,116,838, discloses an artificial bladder for implantation into the bladder's natural position and for connection to the two ureters and to the urethra of a patient. This bladder comprises a hollow elastic ball which can be elastically deformed to an inflated or to a deflated position under the presence of an auxiliary fluid, surrounding a deformable reception chamber for urine; a system of three internal valves, one of which operates in a direction opposite that of the other two; and a device to control the valves thereby controlling the auxiliary fluid. This bladder is complicated and relatively unreliable.

Chevallet, U.S. Pat. No. 3,953,897, discloses an implantable artificial bladder comprising a flexible plastic pouch which relies upon the internal tensions of the pouch wall in combination with external forces, including the force of the patient's abdominal muscles, to empty the pouch completely and rapidly. Chevallet relied upon the peristaltic effect of the ureter to prevent urine from flowing backwards. However, the combination of the internal tension of the artificial bladder wall and the external pressure of the patient's abdominal muscles could likely be greater than the peristaltic pressure of the ureter, particularly upon the discharging of contents of the bladder and therefore could cause urine to flow backwards through the ureters toward the kidneys.

Additionally, the reference bladder chamber is of one piece construction. The configuration of the bladder chamber results in internal capacity that becomes practically negligible upon emptying but not completely empty and necessarily comprises a fold of the chamber, inherently forming a void. The retention of urine resulting from any residual volume can promote infection, disease, or the formation of lithiases, calculi or other concretions.

Rey et al, U.S. Pat. No. 4,311,659, disclose a process for the manufacture of perfect surface state organ prostheses which can be used in the manufacture of artificial bladders and thereby may prevent the formation of various concretions. The one-piece reference bladder, however, in the empty position has a transverse cross-section in the form of two W's lying in opposite direction resulting in residual volume and therefore in retained fluid. Furthermore, backpressure of the Rey et al bladder is such that it preferably requires a urine non-return valve.

Freier, Federated Republic of Germany Patent No. 2,655,034, discloses an artifical bladder comprised of stiff plastics and valves to prevent the return flow of urine through the ureters and toward the kidneys.

Copending, commonly assigned U.S. patent application Ser. No. 07/279,600, filed Dec. 5, 1988, discloses a hard shell constant force stored energy implantable artificial bladder system. A stored energy device is relied upon to empty the bladder, and the disphragm forming the inner chamber folds upon itself.

It is an object of the present invention to provide an implantable artifical bladder soft system which has the compliance, the resistance or the spring rate of a normal bladder and therefore is capable of being completely emptied, which can be filled with only pressure equivalent to the normal peristaltic pressure of normal ureters, which provides virtually no backpressure through the ureter(s) until the bladder is completely full, and which can be discharged either with abdominal pressure, gravity, external pressure or a combination thereof, thereby allowing a patient to function in a nearly normal manner after the removal or the dysfunction of the natural bladder It is a further object of the present invention to provide a method for the collection of, the storage of or the discharge of biological fluids that will allow the patient to function in a nearly normal manner as well.

A primary advantage of the present invention is that the implantable artificial bladder can be emptied completely. A further advantage is that the pressure exerted by the implantable artificial bladder and/or the pressure required to fill or to empty the implantable artificial bladder can be tailored to the individual patient to assure that the back pressure exerted by the implantable artifical bladder does not exceed the peristaltic pressure of the patient's ureter. This assures that there will be no resultant backflow of urine through the ureter(s) to the kidney(s) which would result in damage to those body parts. A still further advantage is that the patient himself can control the discharge of urine by applying the pressure needed to empty the bladder at will.

SUMMARY OF THE INVENTION

Figure 1:
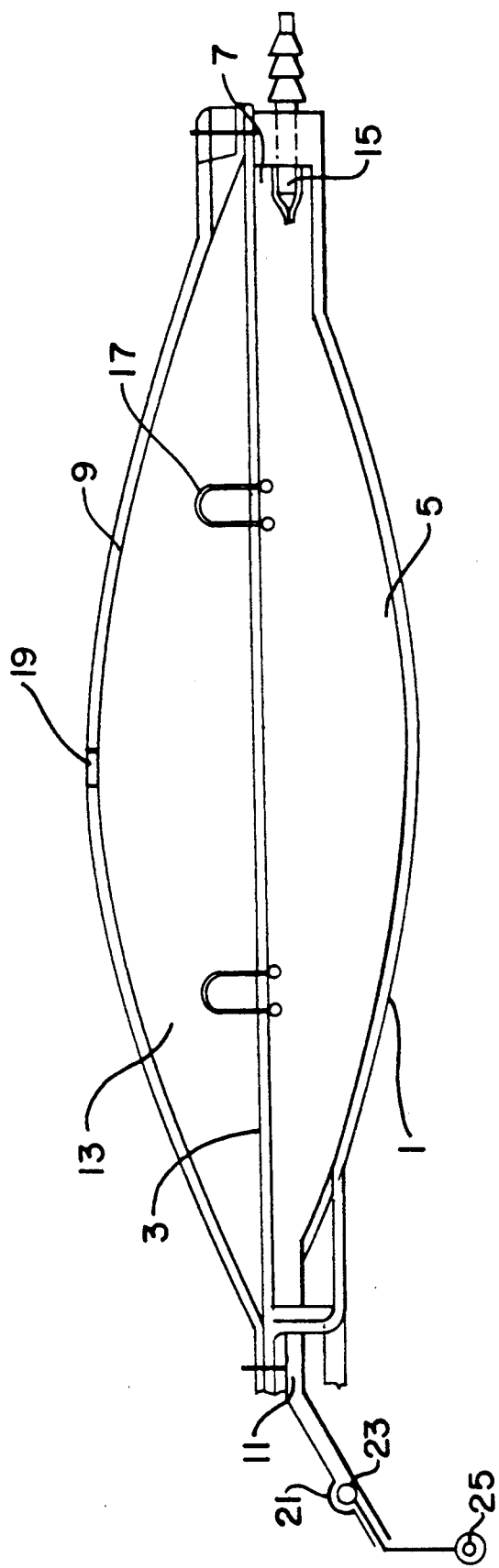
FIG. 1 is an elevation view of an implantable artifical bladder in accordance with the present invention.

According to the present invention, an implantable artifical bladder for the collection of, the storage of, or the discharge of biological fluids is contemplated, comprising (i) a leakproof, at least partially deformation resistant support base comprised of a biocompatible material or a material having a biocompatible surface coating; (ii) a compliant, deformable diaphragm, comprised of a biocompatible material which is the same as or different than the material of (i) or a material having a surface coating of a biocompatible material which is the same as or different than the biocompatible coating material of (i) if it is to contact the natural inner system of a patient, joined to the support base, forming a leakproof inner chamber between the support base and the diaphragm, the diaphragm being deformable between (a) a fully extended position corresponding to the full storage volume of the implantable artificial bladder by pressure about equivalent to the natural peristaltic pressure of at least one ureter of a patient, and (b) a discharged position conforming to the inner surface of the inner chamber formed by the support base by the application of discharge pressure, and completely emptying the inner chamber, leaving no voids or folds, there being nearly zero backpressure at all positions except at the fully extended position; (iii) at least one inlet means in open communication with the inner chamber and adapted to connect to at least one ureter of a patient, to at least one artificial ureter, to a Y-shaped nozzle adapted to connect to both ureters of a patient or to a combination of any of the foregoing; (iv) at least one outlet means in open communication with the inner chamber adapted to connect to the urethra of a patient, to an artificial urethra, or to a combination of the foregoing; optionally (v) a non-elastomeric, outer shell, comprised of a biocompatible material which is the same as or different than the biocompatible material of either (i) or (ii) or a material having a surface coating of a biocompatible material which is the same as or different than the biocompatible coating material of (i) or (ii), surrounding the outer surface of the diaphragm and attached to the support base, forming an outer chamber between said outer shell and said diaphragm, and optionally, having an external vent in open communication with the outer chamber; optionally (vi) a means upstream of the inner chamber for controlling any backflow of biological fluid from the inner chamber to a ureter; optionally (vii) a means downstream of the inner chamber for controlling the rate of flow of biological fluid discharged from the inner chamber; and optionally (viii) a means for anchoring the implantable artificial bladder to a patient.

The invention, in a second major aspect, contemplates a method for the collection of, the storage of or the discharge of biological fluids comprising the steps of attaching an inlet means of the implantable artificial bladder described above to patient's ureter, to an artificial ureter, to a Y-shaped nozzle and attaching a ureter to each of the remaining openings of the Y-shaped nozzle, or to a combination thereof; attaching an outlet means of the implantable artificial bladder to the patient's urethra, to an artificial urethra or to a combination thereof; filling the implantable artificial bladder with biological fluid by the natural peristaltic pressure of the ureter or ureters attached to the inlet means or to the Y-shaped nozzle or a pressure equivalent thereto; storing the biological fluid with nearly zero backpressure until the fully extended position of the diaphragm is reached; and discharging the biological fluid from within the inner chamber through the outlet means and through the patient's urethra or through an artificial urethra by the application of pressure to the diaphragm.

DETAILED DESCRIPTION OF THE INVENTION

FIG. 1 illustrates, in schematic form, a cross-section through an implantable artificial bladder for the collection of, the storage of, or the discharge of biological fluids according to the present invention. The biological fluid preferably is urine.

The leakproof, at least partially deformation resistant support base (1) is comprised of a biocompatible material, i.e. one compatible with the organisms surrounding a natural bladder, or a material having a surface coating of a biocompatible material. Preferably, the support base may be comprised in whole or in part of rigid or semi-rigid materials. The term at least partially deformation resistant is meant to include support bases which may be wholly or partially non-deformable or totally deformable, but are at least in an effective portion of their surface area more resistant to deformation than the deformable diaphragm (3). The effective portion of surface area is that area necessary to assure that the deformable diaphragm upon emptying of the artificial implantable bladder will be able to conform to the support base to achieve the empty position described below. However, if any material other than a rigid material is used, it may be necessary to provide a support frame for the material. Preferably, the support base is comprised of a coated or uncoated structural plastic or, in part, of silicone. Most preferably, the support base is comprised of a poly(vinyl chloride), a poly(etherimide), or a polymer of acrylonitrile/butadiene/styrene, optionally coated with a biocompatible material, including but not limited to silicone or the like.

The degree of deformability of the support base can be varied depending upon the needs of the patient.

A compliant, deformable diaphragm (3), comprised of a biocompatible material or a material having a surface coating of a biocompatible material, particularly if it is not to be surrounded by an optional outer shell and therefore will come into direct contact with the patient's inner system, is attached to the support base to form an inner chamber (5) between the support base (1) and the diaphragm (3). Consequently, the inner surface of the diaphragm and the inner surface of the support base face each other to form the inner surfaces of the inner chamber.

The diaphragm (3) can be attached to the support base (1) by any method known to one of ordinary skill in the art such as adhesive bonding.

The compliant, deformable diaphragm (3) is deformable between two ultimate positions, the first of which is a fully extended position which corresponds to the full volume of the implantable artificial bladder and the second of which is a discharged position corresponding to the completely empty implantable artificial bladder where the volume of the inner chamber is effectively zero.

The compliant, deformable diaphragm (3) generally has a compliancy (i.e. a spring rate or a resistance) similar to that of a natural bladder, thereby allowing a pressure about equivalent to the natural peristaltic pressure of the patient's ureter(s) to fill the implantable artificial bladder with virtually zero backpressure until the fully extended position is reached. Preferably, this pressure will derive directly from the natural peristaltic pressure or the simulated peristaltic pressure of an artificial ureter(s). This eliminates any damage to the patient's ureter(s) or to the patient's kidney(s) due to back pressure in the filling state, the static or storage state, or the discharging state. However, the compliancy or degree of deformability can be adapted to the individual patient's needs such as in a patient with kidney or ureter dysfunction wherein there is either increased or decreased natural peristaltic pressures.

The required compliancy can be determined by any means known to one of ordinary skill in the art including but not limited to finite element analysis. Furthermore, the compliancy need not be uniform throughout the diaphragm but can be further tailored to individual needs by varying the thickness of the diaphragm at different points.

If the support base is deformable in whole or in part, the two sides of inner chamber, i.e. the entire support base should not be equally as easily deformable as the diaphragm. Although portions of the support base may be as easily deformable as the diaphragm, at least a portion must be less easily deformable, i.e. deformation resistant.

The implantable artificial bladder empties by either the diaphragm in effect collapsing alone or the deformable portions of any support base and the diaphragm collapsing together so that neither surface crumbles up individually but preferably retains a flat surface. In the empty or discharged position of the implantable artificial bladder, the compliant, deformable diaphragm (3) fits snuggly against and conforms to the inner surface of the support base (1) without any folds or voids capable of retaining biological fluid, thereby reducing the volume of the inner chamber effectively to zero. Effectively, in this discharged position, the two sides of the inner chamber appear to adhere to one another.

This assures that no biological fluid or a clinically insignificant amount of biological fluid is retained in the empty implantable artificial bladder, thereby minimizing any risk of infection or formation of concretions and the like.

The storage volume of the inner chamber (5) of the implantable artificial bladder can also be adapted to the individual patient, but generally should be small enough to be easily implantable, yet large enough not to require constant or frequent discharge. The volume of the inner chamber (5) of the implantable artificial bladder can be increased or decreased by altering the size of either the support base (1), the diaphragm (3) or a combination of the foregoing. The maximum storage volume of the implantable artificial bladder can vary greatly depending upon the needs of the patient, the pressures desired, and the frequency of discharge required. Preferably, the maximum storage volume will be less than one liter, and most preferably, the maximum storage volume will be less than about 500 ml.

The diaphragm (3) will generally be comprised of a biocompatible material or a material having a coating of a biocompatible material. This material may or may not be the material incorporated in the support base. However, if the outer surface of the diaphragm, i.e. the surface not in contact with the inner chamber, is to be surrounded by an optional outer shell (9) and is thereby prevented from contacting the inner system of the patient's body, it is not necessary that the diaphragm be comprised of such a biocompatible material or coated with such a biocompatible material. Preferably, the diaphragm (3) can be comprised of a silicone elastomer, a collagen, a polyactide, a polysuccinate, a polyoxalate, a flourosilicone, an unsupported silicone, or the like.

There is at least one inlet means (7) in open communication with the inner chamber (5) adapted to connect to at least one ureter of a patient, to an artificial ureter, to a Y-shaped nozzle or to a combination of any of the foregoing. The Y-shaped nozzle may be employed when it is necessary to connect two of the patient's ureters to the artificial implantable bladder. Each of the branches of the Y not directly attached to the inlet means will be connected to one of the patient's ureters or to an artificial ureter. The nozzle eliminates the need for more than one inlet means. An alternative to the Y-shaped nozzle would be more than one inlet means, the number of which corresponds to the number of ureters to be connected. The diameter of the inlet means preferably ranges from about 0.1 to about 0.3 inches in diameter; but could be varied to accommodate insufficient peristaltic pressures supplied by patients suffering from injuries to the ureter(s). Preferably, the inlet means (7) comprises an inlet conduit and an inlet orifice.

Although the inlet means (7) may pass through the support base (1), the diaphragm (3), both of the foregoing at the area at which they are joined or a combination of any of the foregoing, the inlet means (7) preferably passes through the support base (1).

Additionally, there should be at least one outlet means (11) in open communication with the inner chamber adapted to connect to the patient's urethra, to an artificial urethra, or to a combination of the foregoing. It is prefered that this outlet means (11) be about 0.1 to about 0.3 inches in diameter, but the diameter could be varied to increase or to decrease discharge resistance and thereby increase or decrease discharge flow rate and discharge time. The preferred discharge time of an implantable artificial bladder filled with biological fluid is about one minute. Preferably, the outlet means (11) comprises an outlet conduit and an outlet orifice.

Again, although the outlet means (11) may pass through either the support base (1), the diaphragm (3), both of the foregoing at the area at which they are joined, or a combination of any of the foregoing, the outlet means (11) preferably passes through the support base (1).

The optional non-elastomeric outer shell (9) surrounds the outer surface of the diaphragm, i.e. that surface not facing the inner chamber, and is attached to the support base (1), forming an outer chamber (13) between the inner surface of the outer shell and the outer surface of the diaphragm. The outer shell (9) can be comprised of rigid or flexible materials which are biocompatible, or rigid or flexible materials which have a biocompatible surface coating. These materials may be the same as or different than the materials used in the support base (1) and/or the diaphragm (3).

The outer shell (9) may optionally contain a vent (19) in open communication with the outer chamber (13) to allow the passage of displaced and/or external air or fluids into and/or out of the outer chamber. The diameter of the vent can be either fixed or adjustable so that it can be varied to increase or to decrease the rate at which air or fluid can escape the outer chamber (13). If the vent directly communicates with the external environment, any possibility of contamination to the patient due to the introduction of foreign substances through the vent can be overcome by the placement of a sterile but air and/or fluid permeable dressing such as gauze over the opening and can be inherently overcome by designing the vent so that it leads exclusively to a space completely sealed from and inaccessible to the patient's natural system.

A means for the control of any backflow of biological fluids (15) from the inner chamber to the ureter(s) or kidney(s) may optionally be incorporated upstream of the inner chamber. The upstream location may be anywhere from the area of introduction of biological fluid to the inner chamber to the patient's kidney(s), but preferably such location will be at the point of introduction of biological fluid, i.e. the inlet means. This backflow control means (15) can comprise any control means known to one of ordinary skill in the art but most preferably will comprise a check valve. Such a backflow control means will most commonly be necessary in patients whose natural ureters have been damaged and evidence decreased peristaltic pressure insufficient to prevent the backflow of biological fluid naturally or in patients who are subjected to exceptional movement, i.e. vibration or shock, which would place a increased burden on the natural peristaltic pressure of the ureter(s).

Independently, an optional means (21) downstream of the inner chamber may be employed to control the flow of biological fluid exiting the inner chamber. This downstream location may be anywhere from the area of discharge of fluid from the inner chamber to the point at which the biological fluid exits the patient's body. This flow control means can comprise any control means known to one of ordinary skill in the art such as an internal balloon (23) type controlled by an external pump and discharge valve assembly. The internal balloon of an internal balloon type valve is inflated with a pump to prevent discharge by obstructing the discharge channel upon inflation. Discharge is permitted by deflation. The pump may optionally be controlled with a switch (25) either external or internal to the body of the patient. The switch may be actuated by any method known to one of ordinary skill in the art.

The discharge channel is generally comprised of an outlet conduit containing an outlet orifice and the patient's urethra, an artificial urethra, or a combination thereof. When the flow control means is closed, biological fluid can not flow out, and any biological fluid passed into the inner chamber will be collected and stored.

A means for controlling the rate of flow of biological fluids will most commonly be necessary in patients whose natural urethra has been either removed or is dysfunctioning so that the natural sphincter effect of the natural urethra is insufficient to control the flow.

The implantable artificial bladder can be anchored permanently to the patient's body by optional anchoring means (17) attached to the implantable artificial bladder. Preferably, the anchoring means will comprise mesh, foam or a combination of the foregoing which will be suturable and will be placed at various points on the implantable artificial bladder.

Discharge of the inner chamber (5) of the implantable artificial bladder is facilitated by the application of discharge pressure to the outer surface of the diaphragm. Such pressure can be applied by the patient himself, i.e. by the abdominal muscles; by external pressure, including atmospheric pressure; by gravity; or by a combination of the foregoing. The patient's abdominal muscles can be used to apply pressure directly to the diaphragm in the configuration wherein there is no outer shell (9) or indirectly via the outer shell (9) in the configuration wherein the outer shell comprises a flexible material. External pressure can be applied directly to the diaphragm in the absence of an outer shell, or in the presence of an outer shell, through the optional vent to exert a pressure on the diaphragm. External pressure can also be applied indirectly to the diaphragm via direct pressure to the surface of a flexible outer shell. The pressure at which the biological fluid exits the inner chamber preferably is less than the natural peristaltic pressure of the ureter(s) thereby preventing backflow during discharge, but if this is not the case, the optional backflow check valve can be employed to prevent backflow during discharge. Preferably, the maximum discharge time of a full bladder will be about one minute or less.

It may be advantageous in certain patients to supply a signal means to alert the patient when the implantable artifical bladder has been filled so that the patient becomes aware of the necessity to discharge the stored biological fluid.

DESCRIPTION OF THE PREFERRED EMBODIMENT

The following device illustrates the invention and its use. The device is not intended to limit the claims in any manner whatsoever.

EXAMPLE 1

A compliant, deformable diaphragm comprised of silicone, is designed by finite analysis to have a spring rate similar to that of a natural mammalian bladder which is therefore capable of filling with nearly zero back pressure. The diaphragm is joined to a support base comprised of coated structural plastic by adhesive bonding to form an inner chamber having a volume of approximately 250 ml. An inlet means and an outlet means are provided at diametrically opposite positions on the implantable artificial bladder, passing through the diaphragm and the support base at the area of their joinder, to the inner chamber. Anchoring means are provided.

The implantable artificial bladder is implanted into a pig by attaching the natural ureters of the pig to the inlet means and the natural urethra of the pig to the outlet means. The implantable artifical bladder is anchored to the pig by the anchoring means.

Three days after the implant procedure, 370 ml of urine had passed through the free draining bladder system. The implantable artificial bladder continued to function for seven additional days, but was removed due to eventual or progressive failure of the uretal connection.

EXAMPLE 2

An artificial implantable bladder is prepared by the method of Example 1, substituting a support base comprised in part of coated structural plastic and in part of silicone.

The above mentioned patents and test methods are incorporated herein by reference.

Many variations of the present invention will suggest themselves to those skilled in the art in light of the above, detailed description. For example, the size of the vent in the outer shell can be made adjustable to enable it to be used to alter the efficiency of the evacuation of the outer chamber thereby allowing one to adjust the pressure used to fill the inner chamber of the implantable artificial bladder. All such obvious variations are within the full intended scope of the appended claims.

We claim:

1. An implantable artificial bladder for the collection of, the storage of, or the discharge of biological fluid comprising:
   (i) a leakproof, at least partially deformation resistant support base comprised of a biocompatible material or a material having a biocompatible surface coating;
   (ii) a compliant, deformable diaphragm joined to said support base, forming a leakproof inner chamber between said support base and said diaphragm, and deformable between (a) a fully extended position corresponding to the full storage volume of said implantable artificial bladder by pressure about equivalent to the natural peristaltic pressure of at least one ureter of a patient and (b) a discharged position conforming to the inner surface of said inner chamber formed by said support base by the application of discharge pressure, and completely emptying said inner chamber, leaving no voids or folds, there being nearly zero back pressure at all positions except at said fully extended position, said diaphragm optionally comprised of a biocompatible material which is the same as or different than the biocompatible material of (i) or a material having a surface coating of a biocompatible material which is the same as or different than the biocompatible coating material of (i);
   (iii) at least one inlet means in open communication with said inner chamber and adapted to connect to at least one ureter of a patient, to at least one artificial ureter, to a Y-shaped nozzle adapted to connect to both ureters of a patient or to a combination of any of the foregoing;
   (iv) at least one outlet means in open communication with said inner chamber adapted to connect to the urethra of a patient, to an artificial urethra, or to a combination of the foregoing; optionally
   (v) a non-elastomeric outer shell, comprised of a biocompatible material which is the same as or different than the biocompatible material of (i) or (ii) or a material having a surface coating of a biocompatible material which is the same as or different than the biocompatible coating material of (i) or (ii), surrounding the outer surface of said diaphragm and attached to said support base, forming an outer chamber between said outer shell and said diaphragm, and optionally, having an external vent in open communication with said outer chamber; optionally
   (vi) a means upstream of said inner chamber for controlling any backflow of biological fluid from said inner chamber; optionally
   (vii) a means downstream of said inner chamber for controlling the rate of flow of biological fluid discharged from said inner chamber; and optionally,
   (viii) a means of anchoring said implantable artificial bladder to a patient.

2. An implantable artificial bladder as defined in claim 1 wherein said support base comprises a rigid material.

3. An implantable artificial bladder as defined in claim 1 wherein said support base comprises a semi-rigid material supported to maintain its shape.

4. An implantable artificial bladder as defined in claim 1 wherein said support base is comprised of a poly(vinyl chloride), a poly(etherimide), or a polymer of acrylonitrile/butadiene/styrene, optionally coated with a biocompatible material.

5. An implantable artificial bladder as defined in claim 1 wherein said biocompatible coating material in components (i), (ii), (iii) or any combination thereof comprises silicone.

6. An implantable artificial bladder as defined in claim 1 wherein said diaphragm comprises a silicone elastomer, a collagen, a polyactide, a polysuccinate, a polyoxalate, a fluorosilicone or an unsupported silicone, optionally coated with a biocompatible material.

7. An implantable artificial bladder as defined in claim 1 wherein said outer shell comprises a flexible material, a rigid material or a combination thereof.

8. An implantable artificial bladder as defined in claim 1 wherein said inner chamber is adapted to contain urine.

9. An implantable artificial bladder as defined in claim 1 wherein the maximum storage volume of said inner chamber is less than about 500 ml.

10. An implantable artificial bladder as defined in claim 1 wherein said inner chamber in the fully extended position, filled with said biological fluid is adapted to discharge completely in about one minute or less.

11. An implantable artificial bladder as defined in claim 1 wherein said means for controlling the rate of flow comprises an internal balloon valve controlled by an external pump and a discharge valve assembly.

12. An implantable artificial bladder as defined in claim 1 wherein said means for anchoring comprises mesh, foam or a combination thereof.

13. A method for the collection of, the storage of, or the discharge of biological fluid, said method comprising the steps of:
   (a) providing an implantable artificial bladder comprising:

(i) a leakproof, at least partially deformation resistant support base comprised of a biocompatible material or a material having a biocompatible surface coating;

(ii) a compliant, deformable diaphragm joined to said support base, forming a leakproof inner chamber between said support base and said diaphragm, and deformable between (a) a fully extended position corresponding to the full storage volume of said implantable artificial bladder by pressure about equivalent to the natural peristaltic pressure of at least one ureter of a patient and (b) a discharged position conforming to the inner surface of said inner chamber formed by said support base by the application of discharge pressure, and completely emptying said inner chamber, leaving mo voids or folds, there being nearly zero back pressure at all positions except at said fully extended position, said diaphragm optionally comprised of a biocompatible material which is the same as or different than the biocompatible material of (i) of a material having a surface coating of a biocompatible material which is the same as or different than the biocompatible coating material of (i);

(iii) at least one inlet means in open communication with said inner chamber and adapted to connect to at least one ureter of a patient, to at least one artificial ureter, to a Y-shaped nozzle adapted to connect to both ureters of a patient or to a combination of any of the foregoing;

(iv) at least one outlet means in open communication with said inner chamber adapted to connect to the urethra of a patient, to an artificial urethra, or to a combination of the foregoing; optionally (v) a non-elastomeric outer shell, comprised of a biocompatible material which is the same as or different than the biocompatible material of (i) or (ii) or a material having a surface coating of a biocompatible material which is the same as or different than the biocompatible coating material of (i) or (ii), surrounding the outer surface of said diaphragm and attached to said support base, forming an outer chamber between said outer shell and said diaphragm, and optionally, having an external vent in open communication with said outer chamber; optionally (vi) a means upstream of said inner chamber for controlling any backflow of biological fluid from said inner chamber; optionally (vii) a means downstream of said inner chamber for controlling the rate of flow of biological fluid discharged from said inner chamber; and optionally, (viii) a means of anchoring aid implantable artificial bladder to a patient;

(b) attaching said inlet means of said implantable artificial bladder to a patient's ureter, to an artificial ureter, to a Y-shaped nozzle and attaching a ureter to each of the remaining openings of said Y-shaped nozzle, or to a combination thereof;

(c) attaching said outlet means of said implantable artificial bladder to a patient's urethra, to an artificial urethra, of to a combination thereof;

(d) filling said inner chamber of said implantable artificial bladder in the said biological fluid by a pressure equivalent to said natural peristaltic pressure;

(e) discharging said biological fluid from within said inner chamber of said implantable artificial bladder through said outlet means, and through the patient's urethra or through an artificial urethra by the application for pressure to said diaphragm.

14. The method as defined in claim 13 wherein said discharge pressure is applied by abdominal muscles of the patient, by gravity, by an external pressure source, by atmospheric pressure or by a combination of any of the foregoing.

15. The method as defined in claim 13 wherein said support base comprises a rigid material.

16. The method as defined in claim 13 wherein said support base comprises a semi-rigid material supported to maintain its shape.

17. The method as defined in claim 13 wherein said support base is comprised of a poly(vinyl chloride), a poly(etherimide), or a polymer of acrylonitrile/butadiene/styrene, optionally coated with a biocompatible material.

18. The method as defined in claim 13 wherein said biocompatible coating material in components (i), (ii), (iii) or any combination thereof comprises silicone.

19. The method as defined in claim 13 wherein said diaphragm comprises a silicone elastomer, a collagen, a polyactide, a polysuccinate, a polyoxalate, a fluorosilicone or an unsupported silicone, optionally coated with a biocompatible material.

20. The method as defined in claim 13 wherein said outer shell comprises a flexible material, a rigid material or a combination thereof.

21. The method as defined in claim 13 wherein said inner chamber is adapted to contain urine.

22. The method as defined in claim 13 wherein the maximum storage volume of said inner chamber is less than about 500 ml.

23. The method as defined in claim 13 wherein said inner chamber in the fully extended position, filled with said biological fluid, is adapted to discharge completely in about one minute or less.

24. The method as defined in claim 13 wherein said means for controlling the rate of flow comprises an internal balloon valve controlled by an external pump and a discharge valve assembly.

25. The method as defined in claim 13 wherein said means for anchoring comprises mesh, foam or a combination thereof.

* * * * *